US008945238B2

(12) United States Patent
Mosler et al.

(10) Patent No.: US 8,945,238 B2
(45) Date of Patent: Feb. 3, 2015

(54) ARTIFICIAL FOOT

(75) Inventors: Lüder Mosler, Duderstadt (DE); Martin Pusch, Duderstadt (DE); Sven Zarling, Duderstat-Immingerode (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 12/162,190

(22) PCT Filed: Jan. 16, 2007

(86) PCT No.: PCT/DE2007/000057
§ 371 (c)(1),
(2), (4) Date: Jul. 25, 2008

(87) PCT Pub. No.: WO2007/085228
PCT Pub. Date: Aug. 2, 2007

(65) Prior Publication Data
US 2009/0012630 A1 Jan. 8, 2009

(30) Foreign Application Priority Data
Jan. 27, 2006 (DE) .......................... 10 2006 004 132

(51) Int. Cl.
A61F 2/66 (2006.01)
A61F 2/68 (2006.01)
A61F 2/50 (2006.01)

(52) U.S. Cl.
CPC ... A61F 2/66 (2013.01); A61F 2/68 (2013.01); A61F 2002/6664 (2013.01);
(Continued)

(58) Field of Classification Search
CPC .................... A61F 2/66; A61F 2/6607; A61F 2002/6614–2002/6692

USPC ....................................................... 623/47–56
See application file for complete search history.

(56) References Cited

U.S. PATENT DOCUMENTS 4,446,580 A    5/1984  Furuya et al.
5,112,356 A *  5/1992  Harris et al. .................... 623/49
(Continued)

FOREIGN PATENT DOCUMENTS

DE    69905830    9/2003
EP    0988004     3/2000
(Continued)

OTHER PUBLICATIONS

International Search Report for PCT/DE2007/000057, mailed Jul. 5, 2007, 3 pgs.

Primary Examiner — Marcia Watkins
(74) Attorney, Agent, or Firm — Holland & Hart

(57) ABSTRACT

An artificial foot having a longitudinal axis extending from a heel area to a toe area, a length, a width and a height is provided. The artificial foot includes a connection to a lower leg part, an upper supporting structure in the direction of height, an elastic sole structure extending from the heel area to the toe area, an elastic connecting element arranged between the upper supporting structure and the sole structure, and a coupling system. The upper supporting structure is connected to the sole structure approximately in a middle of the foot with respect to its length by means of the coupling system. The coupling system allows a relative tilting motion between the upper supporting structure and the sole structure while keeping a distance between the upper supporting structure and the sole structure in a middle of the coupling system constant, at least while a patient places weight on it when standing.

25 Claims, 8 Drawing Sheets

(52) U.S. Cl.
CPC *A61F 2002/6678* (2013.01); *A61F 2002/5003* (2013.01); *A61F 2002/5009* (2013.01); *A61F 2002/5018* (2013.01); *A61F 2002/503* (2013.01); *A61F 2002/5033* (2013.01); *A61F 2002/6642* (2013.01); *A61F 2002/665* (2013.01); *A61F 2002/6685* (2013.01)
USPC .......................................................... 623/55

(56) References Cited

U.S. PATENT DOCUMENTS

| | | | |
|---|---|---|---|
| 5,116,384 A * | 5/1992 | Wilson et al. .................... | 623/49 |
| 5,290,319 A | 3/1994 | Phillips | |
| 5,387,246 A * | 2/1995 | Phillips ........................... | 623/56 |
| 5,769,896 A * | 6/1998 | Rosendahl et al. .............. | 623/49 |
| 5,993,488 A | 11/1999 | Phillips | |
| 6,875,241 B2 | 4/2005 | Christesen | |
| 2002/0183860 A1 | 12/2002 | Wilkinson et al. | |
| 2004/0162623 A1 | 8/2004 | Phillips | |
| 2005/0267603 A1 | 12/2005 | Lecomte et al. | |

FOREIGN PATENT DOCUMENTS

| | | | |
|---|---|---|---|
| FR | 2048707 | | 3/1971 |
| GB | 2070439 A | * | 9/1981 |
| JP | 52-61999 | | 5/1977 |
| JP | 8-508422 | | 9/1996 |
| JP | 11-277477 | | 12/1999 |
| WO | 91/15171 | | 10/1991 |
| WO | 9422399 A1 | | 10/1994 |
| WO | 9952476 A1 | | 10/1999 |
| WO | 02/02034 | | 1/2002 |
| WO | 2005048887 A1 | | 6/2005 |
| WO | 2005117749 | | 12/2005 |

* cited by examiner

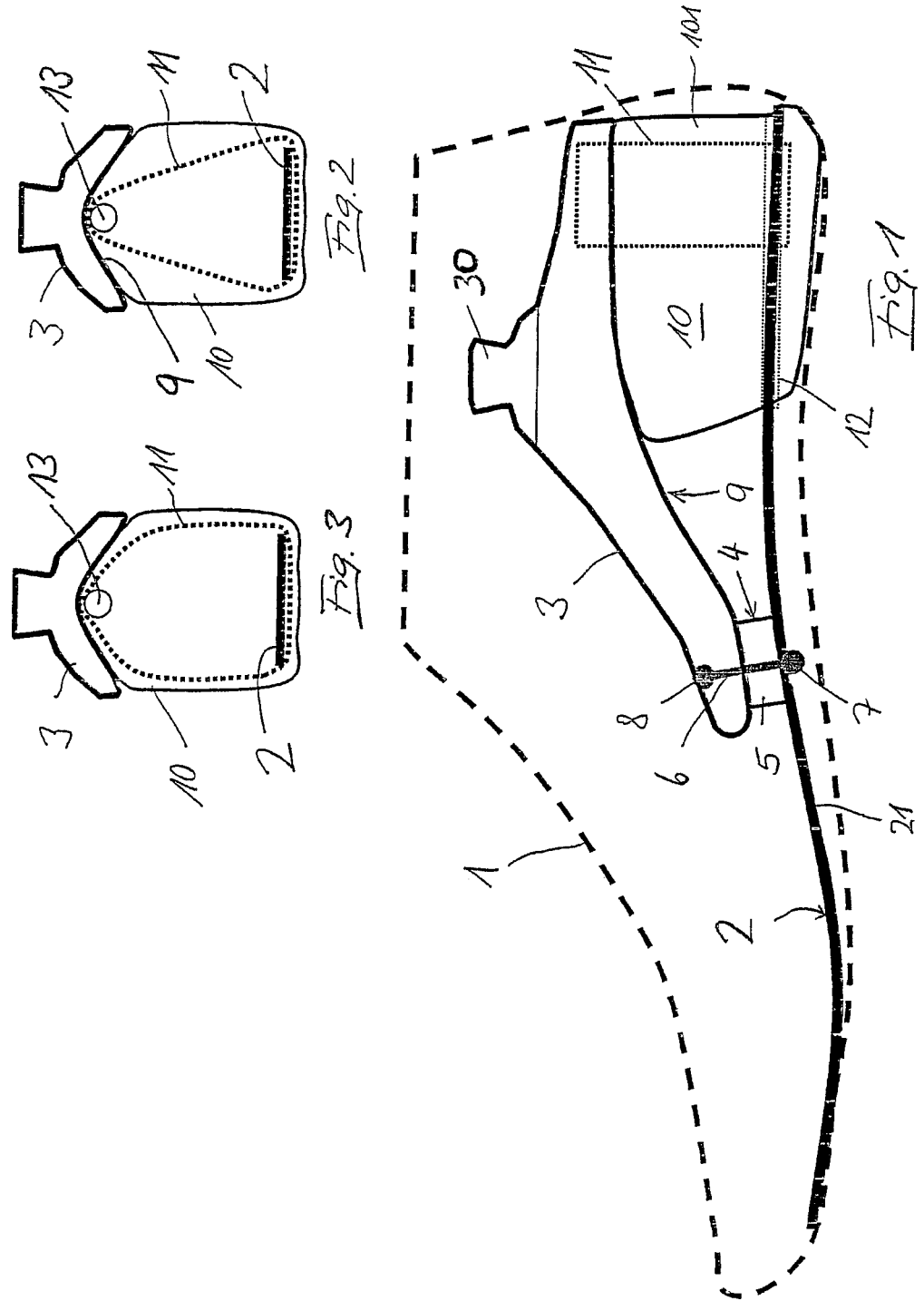

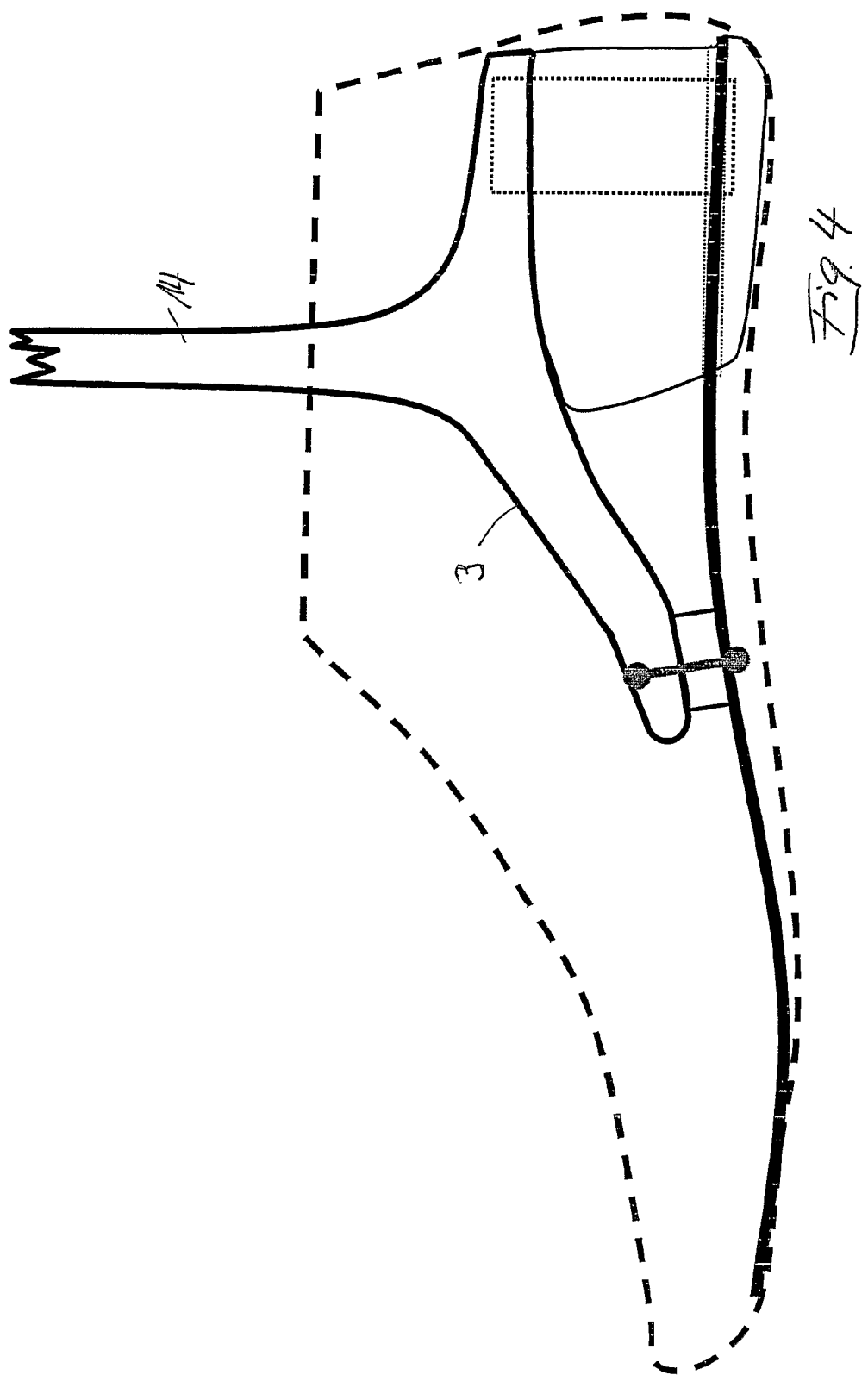

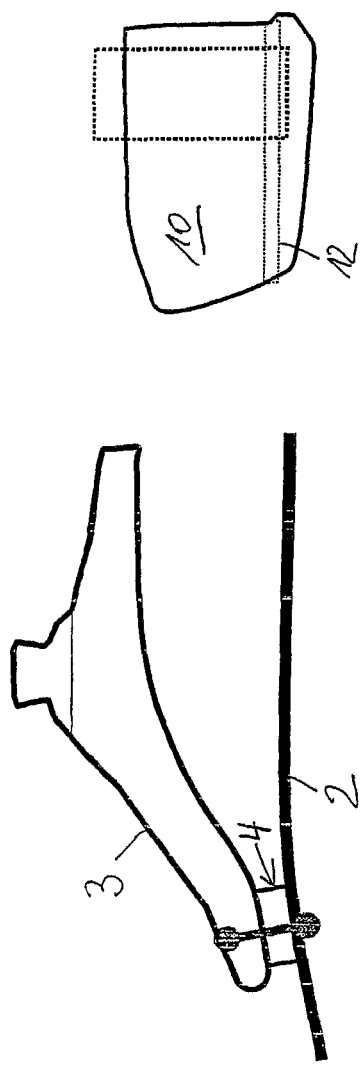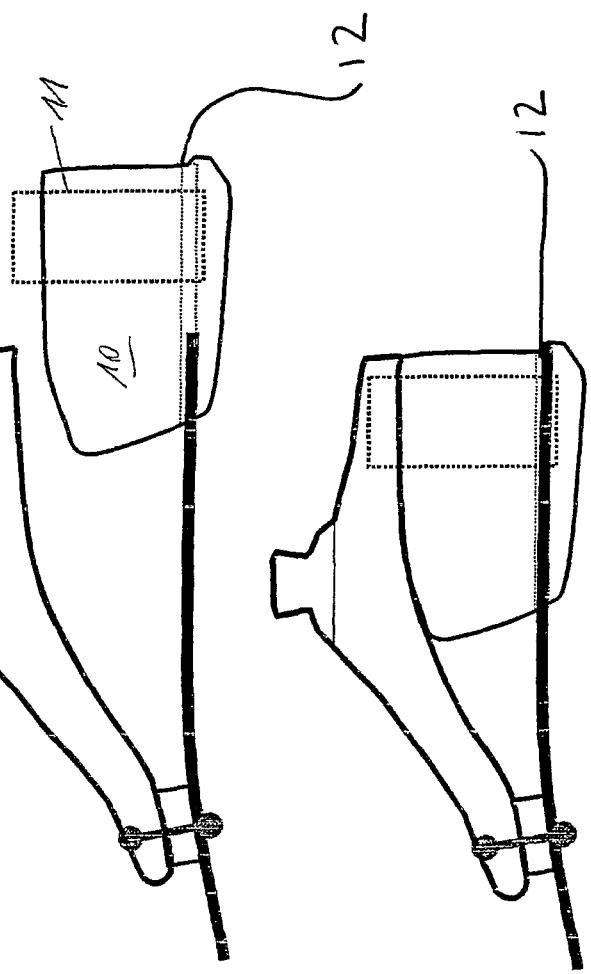

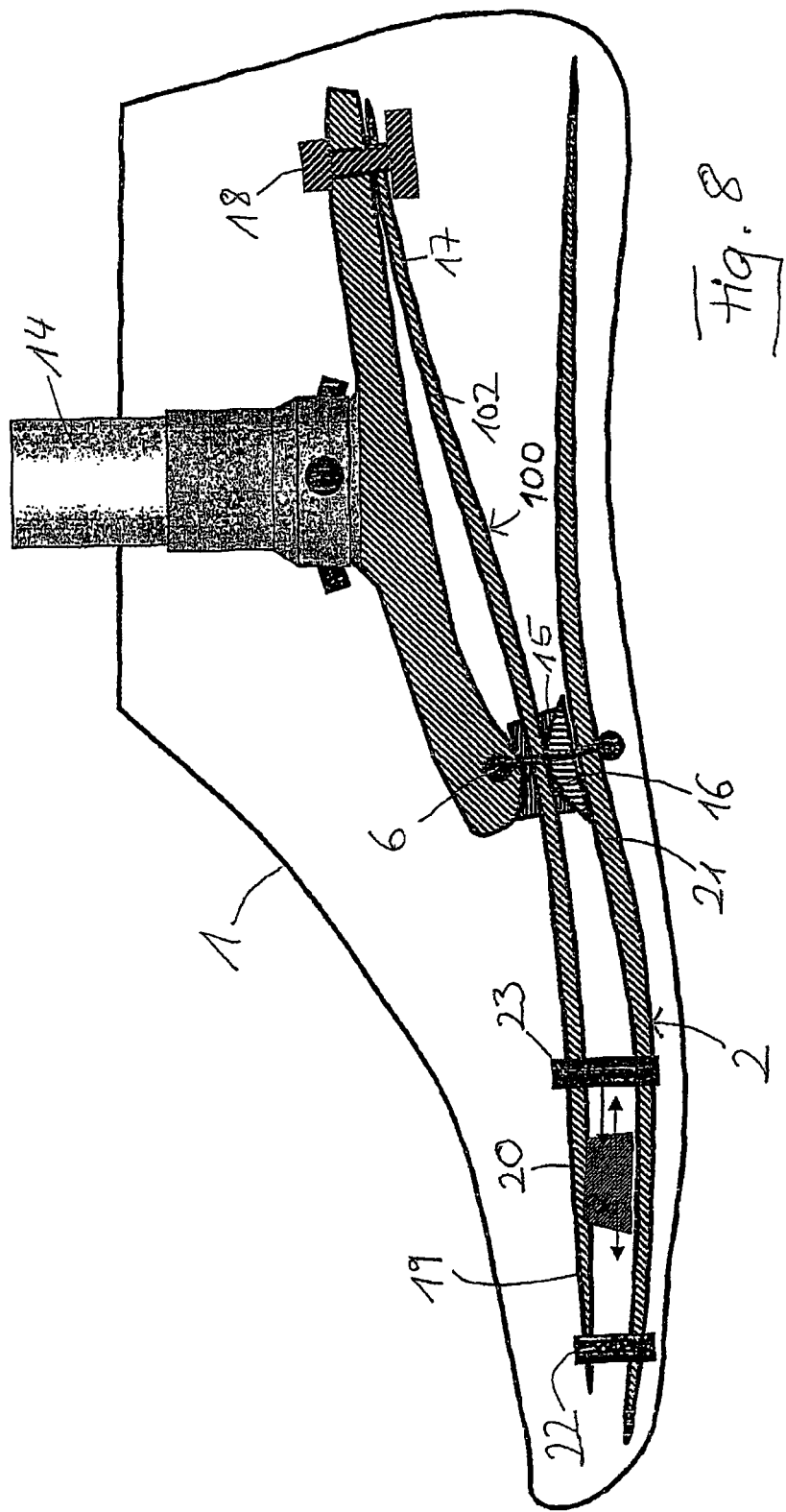

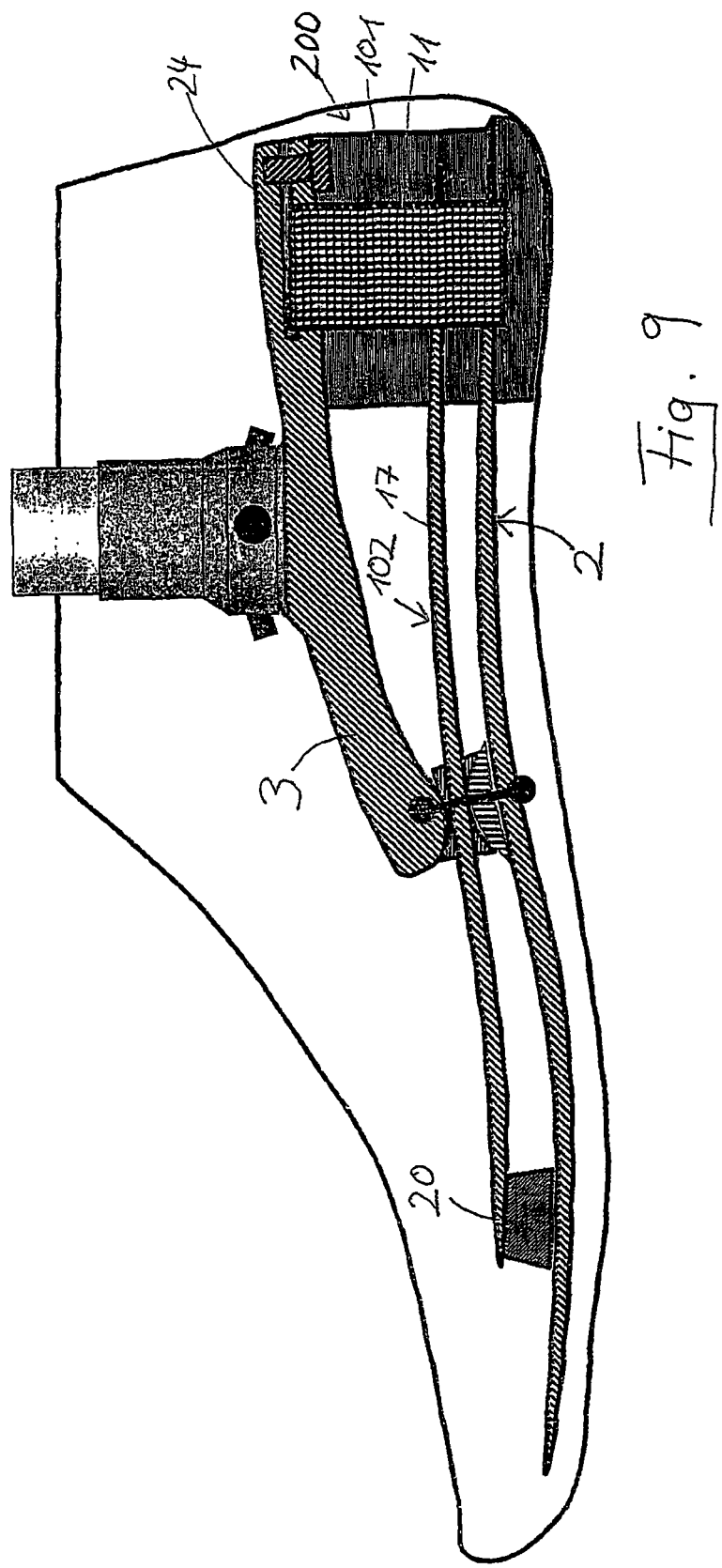

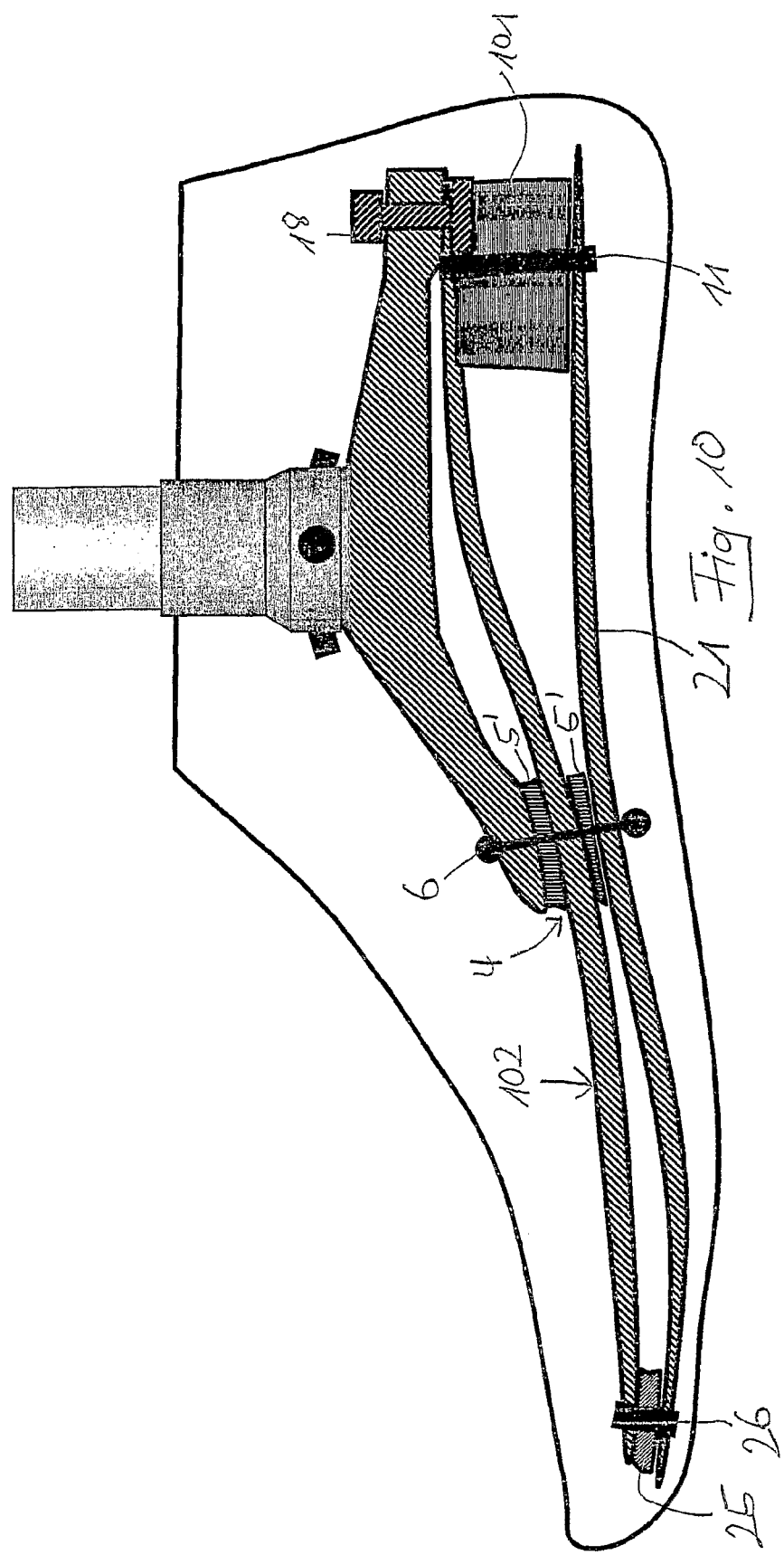

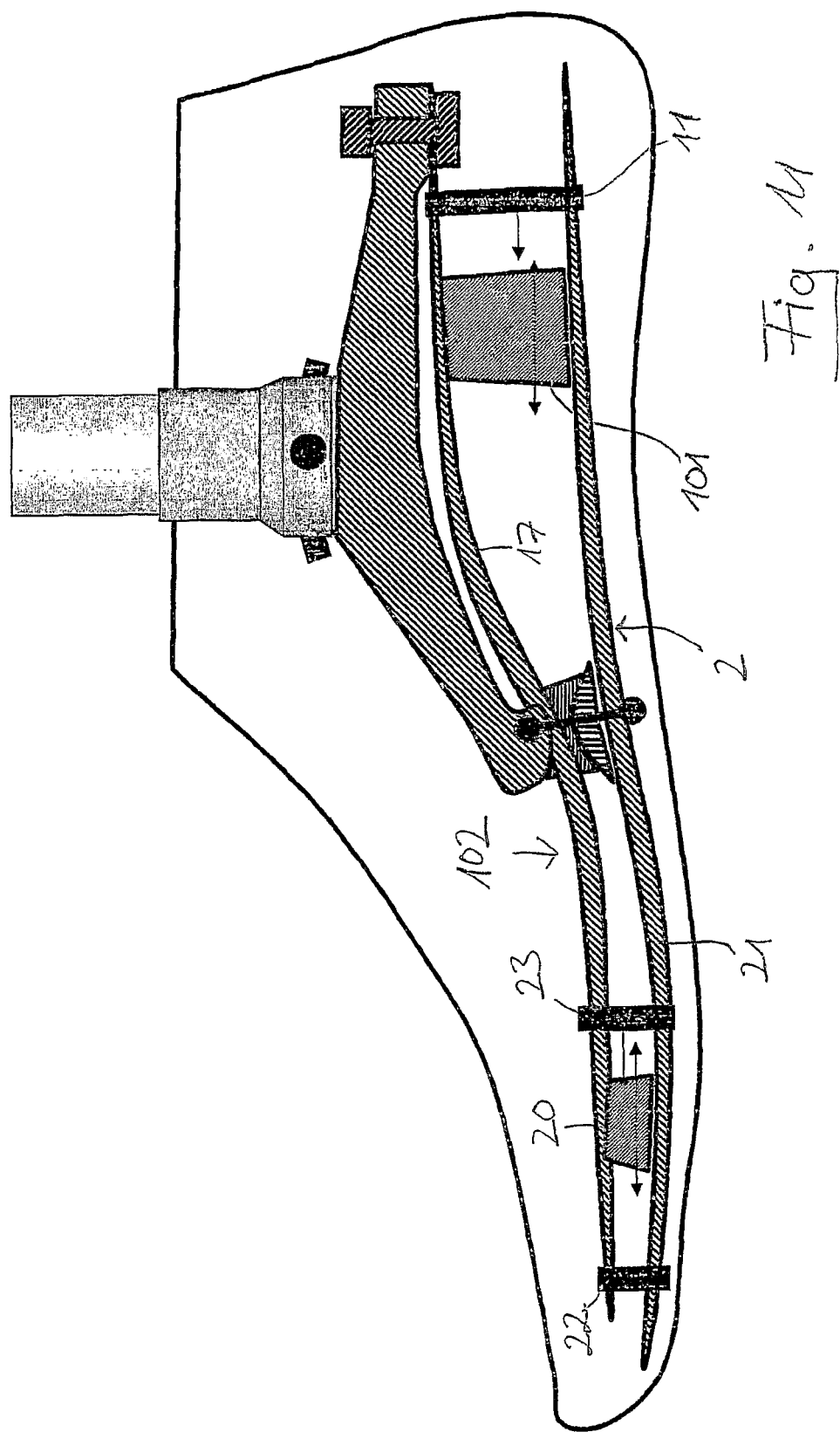

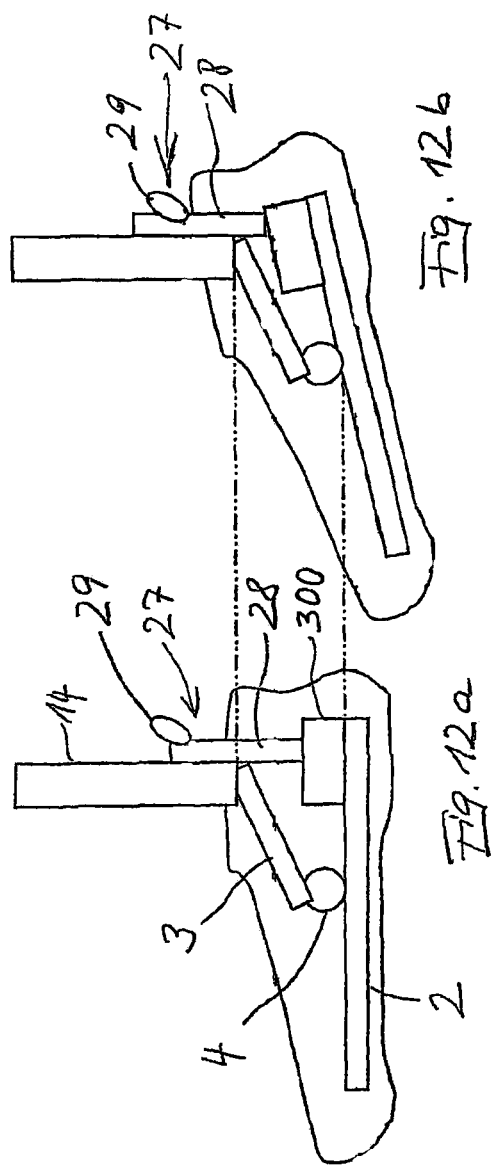

ARTIFICIAL FOOT

CROSS-REFERENCE TO RELATED APPLICATION

This patent application is a national stage application of International Application No. PCT/DE2007/000057 filed Jan. 16, 2007, which claims priority to German Patent No. DE 10 2006 004 132.1, filed on Jan. 27, 2006. The entire content of these applications are hereby expressly incorporated by reference.

TECHNICAL FIELD

The invention relates to an artificial foot with a longitudinal axis extending from a heel area to a toe area, a length, a width and a height, a connection to a lower leg part, a supporting structure uppermost in the direction of height, an elastic sole structure extending from the heel area to the toe area and an elastic connecting element arranged between the upper supporting structure and the sole structure.

The invention further relates to a method for controlling movement of an artificial foot depending on the movement of a lower leg part of a patient.

BACKGROUND

It is known to attach an artificial foot to a lower leg part of a patient such that the foot structure manages without a joint in the region of the natural ankle joint. The flexing action of the foot during walking is accomplished by corresponding elastic formations of the foot structure.

U.S. Pat. No. 5,993,488 discloses a foot structure which includes an upper connection plate, an ankle plate connected solidly to the connection plate and a somewhat bulged sole plate. At the same time the sole plate has approximately the length of the artificial foot and is flexible in a longitudinal direction. The ankle plate is designed shorter and lies substantially parallel to the sole plate. Situated between the ankle plate and the sole plate is a foam block made of relatively firm, though elastic, foam. The foam block has a cross-sectional area for a horizontal cut which corresponds approximately to the cross-sectional area of the ankle plate so that the foam block fills out the interstice between the ankle plate and the sole plate over the entire size of the ankle plate. The parts are connected to one another by adhesion and are secured against delaminating by a band looped around the sole plate and the ankle plate with the interposed foam block. This foot structure causes compression of the foam block, resulting in a shift of the force transfer from the ankle plate to the sole plate correspondingly with the displacement of weight from rear to front. This can be meaningful for a user's gait, and particularly for heel-toe walking on the foot. However it may lead to an unsteady feeling when standing if slight displacements in weight lead to corresponding displacements of the introduction of force between the ankle plate and the sole plate. This gives the patient an unsteady "wobbly" feeling, since there is no defined point for introducing weight forces to the foot construction. This also applies for lateral displacements of weight and for displacements of weight in intermediate directions oblique to the longitudinal axis of the foot.

U.S. Pat. No. 4,446,580 discloses a foot construction in which a tubular lower leg part is connected to a base plate via a hinge joint offset forwards with respect to its longitudinal axis. The lower leg part is guided relative to a guide rod attached flexibly to the base plate, whereby the pivoting motion of the lower leg part around the hinge joint in the base plate is damped by means of plastic dampers. The base plate is solidly anchored in a recess of a sturdy artificial foot. An elastically spring-loaded sole structure and heel strike damping connected thereto are not provided.

SUMMARY

One aim of the present invention is to provide movement of the artificial foot, which on the one hand provides uniform heel-toe walking and on the other hand provides a secure feeling for standing.

An artificial foot of the abovementioned type according to one embodiment of the present invention includes an upper supporting structure connected approximately in the middle of the foot with respect to its length to a sole structure by a coupling system. The coupling system allows a relative tilting motion between the supporting structure and the sole structure and at the same time keeps the distance between the supporting structure and the sole structure in the middle of the coupling system constant, at least as the patient places weight on it when standing.

In another embodiment the multiaxial and flexible movement of the lower leg part is provided by an elastic sole structure having a supporting structure at an introductory point in a middle region relative to the length of the foot such that, at least when the patient is standing, there is no change in distance between the supporting structure and the sole structure at the introductory point. In the heel area, the movement of the elastic sole structure is elastically damped in the direction of the supporting structure and is limited in the direction away from the supporting structure.

According embodiments of the invention the transfer of forces of the lower leg part to the sole structure is made at a defined introductory point at which the supporting structure is multiaxially and flexibly connected to the sole structure to provide a relative tilting motion between the supporting structure and the sole structure when the sole structure is elastically damped. In addition the distance between the supporting structure and the sole structure in the middle of the coupling system at the introductory point remains unchanged, at least when the patient is standing, so that the introduction of force remains unchanged at the introductory point, i.e. in the centre of the foot.

This applies in principle also for heel-toe walking action during walking. Yet it is possible at the same time through reducing the distance via greater compression forces arising from walking at the introductory point to enable slight rearwards displacement of the force introduction point, since the force vector effective between the supporting structure and the sole structure through the tilting motion of the supporting structure forwards migrates slightly rearwards. This leads to comfortable heel-toe walking action and to a feeling of heightened security in heel-toe walking.

In a particular embodiment of the inventive artificial foot, the coupling system includes a hinged arrangement formed, for example, by a material piece which can be compressed by tilting moments on part of its cross-section, but is not compressed in its length by the force occurring from standing. This compression, which causes a reduction in the cylinder length, is permitted only by higher forces, such as those that occur during walking. The material piece particularly has the form of a cylinder of any cross-section and particularly the form of a circular cylinder.

The elastic connecting element is arranged in the inventive artificial foot only in the heel area in one embodiment, and therefore it does not extend uniformly over the entire length of the supporting structure. The elastic connecting element can be a bent leaf spring or other spring system, such as an elastic pad made of plastic foam material.

A limiting device of the elastic connecting element is a flexible and inelastic band which is tensible in the case of increasing distance of the upper supporting structure from the sole structure, such as in particular during heel-toe walking by the artificial foot across the toe region.

The flexible band may be guided with deflection through the elastic pad so that elastic displacement of material of the elastic pad tenses the band. This makes it possible to control the forefoot resistance during heel-toe walking via the forefoot by guiding the flexible band through the elastic pad or respectively around the elastic pad and thus to adapt it to the needs of the patient.

In one embodiment, the upper supporting structure includes a rigid material, or at least a material having an elasticity less than the elasticity of the sole structure.

In one embodiment of the inventive foot, the hinged arrangement is arranged on the toe-side end of the upper supporting structure. In other words, the upper supporting structure ends appropriately on the hinged arrangement.

In another embodiment, the upper supporting structure has an underside which rises from the toe-side end relative to the sole structure so that the heel-side end is a greater distance from the sole structure than in the region of the coupling system.

For easy installing of the inventive artificial foot, the elastic pad has a horizontal slot into which the sole structure is inserted. In one embodiment, the flexible band forming the limiting device is looped around the underside of the sole structure. The upper supporting structure can then have a lug around which the band can loop on its top side.

The inventive artificial foot also allows a stable standing function even with different heel heights for a shoe worn on the artificial foot by providing a lockable height-adjustment device, with which the distance between the sole structure and the upper supporting structure can be adjusted, in terms of power flow in series with the elastic connecting element. The angle between the upper supporting structure and the sole structure can be adjusted by way of the height-adjustment device, whereby adaptation to different heel heights is possible.

BRIEF DESCRIPTION OF THE DRAWINGS

The invention will be explained hereinbelow in greater detail by means of exemplary embodiments illustrated in the diagram, in which:

FIG. 1 shows a schematic illustration of the structure of an inventive artificial foot in a first embodiment;

FIG. 2 shows an exemplary embodiment for an arrangement of a flexible, however inelastic band serving as a limiting device;

FIG. 3 shows a modified arrangement of the band for controlling forefoot resistance during heel-toe walking;

FIG. 4 shows a schematic illustration according to FIG. 1 for a second embodiment of an inventive artificial foot;

FIGS. 5 to 7 show three phases for fitting the artificial foot according to FIG. 1;

FIG. 8 shows a schematic illustration of a third embodiment of an inventive artificial foot;

FIG. 9 shows a schematic illustration of a fourth embodiment of an inventive artificial foot;

FIG. 10 shows a schematic illustration of a fifth embodiment of an inventive artificial foot;

FIG. 11 shows a schematic illustration of a sixth embodiment of an inventive artificial foot; and FIGS. 12a and 12b shows two schematic illustrations of a seventh embodiment of an inventive artificial foot, provided with a height-adjustment device.

DETAILED DESCRIPTION

FIG. 1 illustrates a cosmetic sheath 1 of an artificial foot in dashes. A sole structure 2 extends essentially over the entire length of the foot. The sole structure 2, when viewed from below in a toe area, has a convex arching which transitions approximately in the middle of the foot into a concave arching that may extend as far as a heel area. The sole structure 2 in the illustrated exemplary embodiment includes a flat, striated, long stretched-out sole spring 21. Approximately in the middle of the foot the sole structure 2 is connected to a front end of a supporting structure 3 via a coupling system formed by a hinged arrangement 4. The hinged arrangement 4 includes a material piece 5 in the form of a plastic cylinder, supported by a lower front end on the sole structure 2 and by an upper front end on an underside of the supporting structure 3. In the illustrated embodiment the hinged arrangement 4 is complemented by a pin arrangement 6 which has ballpoint attachments 7, 8 at both its ends. The ballpoint attachments 7, 8 are supported on the sole structure 2 on the one hand and on the supporting structure 3 on the other hand. The ballpoint attachments 7, 8 increase the stability of the connection between the supporting structure 3, the cylinder 5 and the sole structure 2, without hindering relative tiltability of the supporting structure 3 relative to the sole structure 2.

The relative tiltability results from an elastic configuration of the cylinder 5. The cylinder 5 can be pressed in by inclinations of the supporting structure 3 relative to the sole structure 2 on part of its cross-section by the weight forces of a patient wearing the artificial foot. As a result, the opposite part of the cylinder 5 diametrical in cross-section expands such that the average height of the cylinder 5, and therefore the resulting average distance between the supporting structure 3 and the sole structure 2 in the region of the hinged arrangement 4, remains constant.

A lessening of the middle distance is permitted due to forming the cylinder 5 to be pressed in only by higher forces, such as those that occur on the hinged arrangement 4 with heel-toe walking of the foot during walking.

The supporting structure 3 has an underside 9, which rises from the hinged arrangement 4 to the heel area relative to the sole structure 2, so that the distance between supporting structure 3 and sole structure 2 increases from the hinged arrangement 4 to the heel area. An elastic connecting element 10, in the form of an elastic pad 101 is arranged, in the heel area between the supporting structure 3 and the sole structure 2. The elastic pad 101 includes a limiting device in the form of a flexible band 11, which fixes a maximum distance between the supporting structure 3 and the sole structure 2 in the region of the band 11, as shown in greater detail in FIGS. 2 and 3.

The supporting structure 3 has on its top side an adjusting trunnion 30, to which a connection to a corresponding lower leg part of a lower leg prosthesis can be attached.

FIG. 2 shows that the flexible, but inelastic, band 11 is positioned inside the elastic pad 101 and loops around the underside of the sole structure 2. For receiving the sole structure 2 the elastic pad 101 is provided with a continuous horizontal slot 12, illustrated in FIG. 1 by dots. The endless band 11 loops around a cylindrical lug 13 on the underside of the supporting structure 2.

FIG. 2 shows the tensed state of the band 11 at the maximum distance between the supporting structure 3 and the sole structure 2. It is evident that with a heel strike the elastic pad 101 can compress, to cause the flexible band 11 to transition from the tensed state into a slack state, with a wrinkle. By subsequently expanding the elastic pad 101 or by loading the forefoot area of the sole structure 2, the flexible band 11 is returned to the tensed position illustrated in FIG. 2.

FIG. 2 further discloses that the underside 9 of the supporting structure 3 has a roof-like design and that the elastic pad 101 includes a corresponding roof-like top side that rests on the roof-like underside 9 of the supporting structure 3 and can be adhesively bonded thereon.

In the exemplary embodiment illustrated in FIG. 3, the band 11 runs between the sole structure 2 and the lug 13 inside the elastic pad 101 along a bent line. To limit the maximum distance between the supporting structure 3 and the sole structure 2, the band 11 is tensed in such a way that it forms a straight line between the lug 13 and the lateral edges of the sole structure 2. For this to happen, the band 11 compresses areas of the elastic pad 101 to the side so that elastic damping occurs with increasing distance between the sole structure 2 and the supporting structure 3 caused by forefoot loading of the sole structure 2. The flexing action of the forefoot of the sole structure 2 is thus possible with increased resistance to control the forefoot resistance of the artificial foot via the arrangement of the flexible band 11.

The embodiment illustrated in FIG. 4 differs from the embodiment illustrated in FIG. 1 only in that the supporting structure 3 transitions in one piece into a lower leg part 14, such that no connection needs to be made between the lower leg part 14 and the supporting structure 3.

The inventive artificial foot is assembled by connecting the supporting structure 3 to the sole structure 2 via the hinged arrangement 4, resulting in a heel area open to the rear. The elastic pad 101 is inserted into the conically opened interstice between the supporting structure 3 and the sole structure 2 by pushing the sole structure 2 by its rear end into the slot 12 serving as a recess, as is shown in FIG. 6 in an intermediate position. As the elastic pad 101 is pushed in further, the flexible band 11, which projects from the top side of the elastic pad 101 by a loop, is pushed over the lug 13 (not illustrated in FIGS. 5 to 7). After the elastic pad 101 is fully slid on when the limiting device in the form of the closed circular flexible, but inelastic, band 11 is being installed, the elastic pad 101 can be connected via a hardening adhesive to the supporting structure 3, and where necessary to the sole structure 2.

The effect of the roof-like configuration of the underside 9 of the supporting structure 3 and the corresponding roof-like configuration of the top side of the elastic pad 101 is to automatically center the elastic pad 101 in connection with the guiding caused by inserting the sole structure 2 into the take-up slot 12.

As in FIG. 1 and FIG. 4, FIG. 7 shows that the part of the elastic pad 101 protruding beneath the sole structure 2 can serve as a damper for the sole structure 2 during heel strike. Any shaping of the elastic pad 10 on this underside favors the heel-toe walking action during heel strike.

The hinged arrangement formed by the cylinder 5 in the illustrated exemplary embodiments can also be designed differently, for example in the form of a universal ball joint, as shown in FIGS. 12a and 12b, which cooperates with a corresponding ball socket. This would form a tiltable connection between the supporting structure 3 and the sole structure 2 without altering the distance between the supporting structure 3 and the sole structure 2 at the introductory point of force in the region of the hinged arrangement 4 when the patient stands. Due to the higher forces during walking, for example, the universal ball joint can be made of a plastic indented by these forces, or hard rubber.

A third embodiment of an inventive artificial foot illustrated in FIG. 8 has an elastic connecting element 100 between the supporting structure 3 and the sole structure 2 in the form of a control spring 102. The control spring 102 is designed as a two-armed spring part with a middle piece 15 that forms part of the hinged arrangement 4. The middle piece 15 is provided on its top side with a concave arching, in which a corresponding convex arching of the toe-side end of the supporting structure 3 rests. The underside of the middle piece 15 is likewise arched concavely to the underside and rests on a corresponding convex arching of a plastic damper 16. The hinged arrangement 4 is held together by a pin arrangement 6.

The control spring 102 is connected to a heel-aligned arm 17 at the heel-side end of the supporting structure 3 by means of a fixing screw 18. A toe-aligned arm 19 of the control spring 102 runs approximately parallel to the toe-side end of a sole spring 21. In this area the toe-aligned arm 19 of the control spring 102 and the sole spring 21 are connected via an elastic damper 20 and two flexible, but inelastic retaining straps 22, 23 are arranged on both sides of the damper 20.

With heel strike during walking the heel-aligned arm 17 of the control spring 102 is deformed elastically downwards, i.e. in the direction of the heel-side end of the sole spring 21. Apart from the deforming of the heel-aligned arm 17 damping the heel strike, upwardly directed torque occurs on the toe-aligned arm 19 of the control spring 102. While the foot performs plantar flexion with respect to the lower leg part 14, the toe area of the foot is raised by the toe-aligned arm 19 of the control spring 102, making heel-toe walking of the foot easier.

The flexible retaining strap 23, arranged between the middle piece 15 and the elastic damper 20, is adjustable in a longitudinal direction similar to the elastic damper 20, as indicated by the arrows in FIG. 8. A shift of the flexible retaining strap 23 (illustrated here in the middle) between the middle piece 15 and the toe-side end of the sole structure 2 leads to reduction of the resulting hardness of the heel-aligned arm 17 of the control spring 102. The heel strike is damped more softly. The position of the elastic damper 20 acts independently as adjusting means of the forefoot hardness of the sole structure 2. The forefoot becomes stiffer as the elastic damper 20 approaches the forefoot tip. The sole spring 21 and the control spring 102 are synchronized such that desired plantar flexion occurs during heel strike.

In a fourth exemplary embodiment illustrated in FIG. 9, the elastic connecting element 200 is again formed substantially by the elastic pad 101 in the heel area. The flexible band 11, which limits the maximum distance between the rear end of the supporting structure 3 and the heel-side end of the sole structure 2, is looped through a rearwards open slot 24 of the supporting structure 3. The control spring 102 projects into the elastic pad 101 with its heel-aligned arm 17. The control spring 102 substantially forms part of the sole structure 2. The forefoot rigidity can be adjusted by the sizing and positioning of the elastic damper 20.

In a fifth embodiment illustrated in FIG. 10, the control spring 102 is connected to the heel-side end of the supporting structure 3 by its heel-side end again via the fixing screw 18. Also, the elastic pad 101 for heel strike damping is arranged between the supporting structure 3 or respectively the heel-aligned arm 17 of the control spring 102. Movement augmenting the distance between the supporting structure 3 and the sole structure 2 in the heel area is restricted by the flexible band 11.

Similarly to exemplary embodiment illustrated in FIG. 1, the hinge joint 4 is formed by a pin arrangement 6 and two, plastic cylinders 5', which are arranged between the support structure 3 and the control spring 102 on the one hand and between the control spring 102 and the sole spring 21 on the other hand.

In this embodiment, the front ends of the control spring 102 and of the sole spring 21 are connected to one another by an elastic damper 25 and a flexible, but inelastic, retaining strap 26. The control spring 102 and the sole spring 21 are synchronized such that plantar flexion occurs during heel strike. The heel stiffness can be adjusted by exchanging the elastic pad 101.

FIG. 11 shows an exemplary embodiment modified relative to FIG. 10, in which improved adjustment options are provided. As in the exemplary embodiment illustrated in FIG. 8, shifting the flexible retaining strap 23 to the heel-side end of the sole structure 2, causes damping by the heel-aligned arm 17 of the control spring 102 to be softer. The shift of the elastic damper 20 in a longitudinal direction causes a change in the forefoot hardness, whereby a shift of the elastic damper 20 to the toe end sets a greater hardness of the forefoot. Shifting of the plastic pad 101 in a longitudinal direction and of the associated flexible band 11 further influences the damping of the heel strike on the one hand and the forefoot hardness on the other hand, because the length of the effective heel-aligned arm 17 of the two-armed control spring 102 is altered.

FIGS. 12a and 12b schematically illustrate a seventh embodiment of an inventive artificial foot. The illustrations schematically show the sole structure 2, the hinge joint 4, the upper supporting structure 3 and the lower leg part 14. The lower leg part 14 is connected rigidly to the upper supporting structure 3. In the heel area the elastic connecting element 300 is provided, in particular in the form of a heel buffer. This is connected to the upper supporting structure 3 or respectively the lower leg part 14 not directly, but rather via a die 28 which is arranged to shift relative to the lower leg part 14 and can be fixed by means of a schematically illustrated locking member 29.

FIG. 12a shows a seventh embodiment in a bare-foot position without additional heel height from a shoe. FIG. 12b shows by way of contrast that the sole structure 2 has been reduced in its distance from the lower leg part 14 or respectively the upper supporting structure 3. This alters the angular setting of the sole structure 2 relative to the lower leg part 14 and the upper supporting structure 3 such that adaptation to a heel height of a shoe is guaranteed. It is readily evident that adaptations to different heel heights are possible via various adjustments of the die 28 relative to the lower leg part 14 or respectively to the upper supporting structure 3.

The inventive construction enables a comfortable flexing action with damped tilting motions corresponding to the natural foot, without causing uncertainty for the patient due to changes in the force introduction point when standing. Due to the unchanged average distance between the supporting structure 3 and the sole structure 2 in the region of the hinged arrangement 4, the inventive constructions leave the force introduction point unaltered, in any case whenever the patient is standing. An advantageously minimal back displacement of the force introduction point for heel-toe walking can be implemented during walking.

The invention claimed is:

1. An artificial foot, comprising:
    a connection configured to connect with a lower leg part;
    an upper support structure projecting downwardly and forwardly from the connection;
    an elastic sole structure extending from a heel area to a toe area of the artificial foot;
    the upper support structure comprising a first material, the sole structure comprising a second material, the first material being less elastic than the second material;
    an elastic element arranged between the upper support structure and the elastic sole structure;
    a coupling system arranged at a toe-side end of the upper support structure and that connects the upper support structure to the sole structure at a middle region along a length of the artificial foot at a location forward of the connection, wherein the coupling system provides lateral tilting and medial tilting of the upper support structure relative to the sole structure with direct contact between the upper support structure and coupling system while limiting forward tilting and rearward tilting of the upper support structure relative the sole structure when standing and walking to maintain a constant distance between the upper support structure and the sole structure in a middle of the coupling system.

2. The artificial foot of claim 1, wherein the coupling system provides tilting in all directions of the upper support structure relative the sole structure when walking.

3. An artificial foot, comprising:
    a connection configured to connect with a lower leg part;
    an upper support structure projecting downwardly and forwardly from the connection;
    an elastic sole structure extending from a heel area to a toe area of the artificial foot;
    the upper support structure comprising a first material, the sole structure comprising a second material, the first material being less elastic than the second material;
    an elastic element arranged between the upper support structure and the elastic sole structure;
    a coupling system arranged at a toe-side end of the upper support structure and that connects the upper support structure to the sole structure at a middle region along a length of the artificial foot at a location forward of the connection, wherein the coupling system provides lateral tilting and medial tilting of the upper support structure relative to the sole structure while limiting forward tilting and rearward tilting of the upper support structure relative the sole structure with direct contact between the support structure and coupling system when standing and walking to maintain a constant distance between the upper support structure and the sole structure in a middle of the coupling system, and provides tilting in all directions of the upper support structure relative the sole structure when walking.

4. An artificial foot with a longitudinal axis extending from a heel area to a toe area, a length, a width and a height comprising:
    a connection adapted to receive a lower leg part;
    an upper support structure projecting downwardly and forwardly from the connection;
    an elastic sole structure extending from the heel area to the toe area;
    the upper support structure comprising a first material, the sole structure comprising a second material, the first material being less elastic than the second material;
    an elastic element arranged between the upper support structure and the elastic sole structure; and a coupling system which is arranged at a toe-side end of the upper support structure and that connects the upper support structure to the sole structure at a middle region along the length of the artificial foot thereby determining a distance between the upper structure and the sole structure when no weight is placed on the artificial foot, wherein the coupling system provides for a multiaxial relative tilting motion between the upper support structure and the sole structure with direct contact between the upper support structure and coupling system in at least a lateral direction and a medial direction while maintaining the determined distance between the upper support structure and the sole structure in a middle of the coupling system constant when a user places weight on the coupling system in a standing position such that transfer of forces from the lower leg part to the sole structure in a portion of the artificial foot where the coupling system connects the upper support structure to the sole structure is maintained at an introductory point established by the coupling system.

5. The artificial foot as claimed in claim 4, wherein the coupling system is formed by a material piece which can be compressed by tilting moments on a part of a cross-section of the material piece.

6. The artificial foot as claimed in claim 4, wherein the coupling system is compressed by higher forces to lessen a distance in the middle of the coupling system.

7. The artificial foot as claimed in claim 4, wherein the elastic element includes an elastic pad.

8. The artificial foot as claimed in claim 7, wherein the elastic element includes a limiting device limiting a distance between the upper supporting structure and the sole structure.

9. The artificial foot as claimed in claim 8, wherein the limiting device includes a flexible band which is tensible with increasing distance between the upper supporting structure and the sole structure.

10. The artificial foot as claimed in claim 9, wherein the flexible band is guided with deflection by the elastic pad so that elastic displacement by material of the elastic pad is required to tense the band.

11. The artificial foot as claimed in claim 9 wherein the flexible band is looped around an underside of the sole structure.

12. The artificial foot as claimed in claim 11, wherein a lug which can be looped around by the flexible band on a top side of the lug is arranged on the upper supporting structure.

13. The artificial foot as claimed in claim 7, wherein the elastic pad has a horizontal slot through which the sole structure is pushed.

14. The artificial foot as claimed in claim 7, wherein the elastic pad is arranged adjustably in a longitudinal direction.

15. The artificial foot as claimed in claim 4, wherein the upper supporting structure is formed from a rigid material.

16. The artificial foot as claimed in claim 4, wherein the upper supporting structure has an underside which increases in distance from a toe-side end to a heel-side end relative to the sole structure so that at the heel-side end, the underside is at a greater distance from the sole structure than a region of the coupling system.

17. The artificial foot as claimed in claim 16, wherein the underside of the supporting structure has a roof-like heel area.

18. The artificial foot as claimed in claim 17, wherein an elastic pad with a roof-like top side rests on the roof-like heel area of the underside of the supporting structure.

19. The artificial foot as claimed in claim 4, wherein the elastic element has a control spring with a heel-aligned arm.

20. The artificial foot as claimed in claim 4 wherein a toe-aligned arm of a control spring forms part of the sole structure, and wherein the toe-aligned arm is connected to a front end of a sole spring of the sole structure.

21. The artificial foot as claimed in claim 20, wherein the connection of the toe-aligned arm to the sole spring occurs via an elastic damper.

22. The artificial foot as claimed in claim 21, wherein flexible retaining straps limiting a distance between the sole spring and the toe-aligned arm are arranged in a longitudinal direction on both sides of the elastic damper.

23. The artificial foot as claimed in claim 4, wherein a lockable height-adjustment device having power flow in series with the elastic connecting element, with which a distance between the sole structure and the upper supporting structure can be adjusted.

24. The artificial foot as claimed in claim 4, wherein the coupling system connects the upper support structure to the sole structure at a midpoint along a length of the artificial foot, the midpoint being within the middle region.

25. An artificial foot with a longitudinal axis extending from a heel area to a toe area, a length, a width and a height comprising:
a connection adapted to receive a lower leg part;
an upper support structure projecting downwardly and forwardly from the connection;
an elastic sole structure extending from the heel area to the toe area;
the upper support structure comprising a first material, the sole structure comprising a second material, the first material being less elastic than the second material;
an elastic element arranged between the upper support structure and the elastic sole structure; and
a coupling system arranged at a toe-side end of the upper support structure and that connects the upper support structure to the sole structure at a middle region along the length of the artificial foot thereby determining a distance between the upper structure and the sole structure when no weight is placed on the artificial foot, wherein the coupling system provides for a relative tilting motion between the upper support structure and the sole structure with direct contact between the upper support structure and coupling system in at least a lateral direction and a medial direction while maintaining the determined distance between the upper support structure and the sole structure in a middle of the coupling system constant when a user places weight on the coupling system when standing such that transfer of forces from the lower leg part to the sole structure in a portion of the artificial foot where the coupling system connects the upper support structure to the sole structure is maintained at an introductory point structure and the sole structure in the middle of the coupling system changes when a user places an increased weight on the coupling system when walking.

* * * * *

UNITED STATES PATENT AND TRADEMARK OFFICE
CERTIFICATE OF CORRECTION

| | | |
|---|---|---|
| PATENT NO. | : 8,945,238 B2 | Page 1 of 1 |
| APPLICATION NO. | : 12/162190 | |
| DATED | : February 3, 2015 | |
| INVENTOR(S) | : Mosler et al. | |

It is certified that error appears in the above-identified patent and that said Letters Patent is hereby corrected as shown below:

On the title page, item (54) and in the specification, column 1, line 1, the title, delete "ARTIFICIAL FOOT" insert --ARTIFICIAL FOOT AND METHOD FOR CONTROLLING THE MOVEMENT THEREOF--.

Signed and Sealed this
Nineteenth Day of May, 2015

Michelle K. Lee
*Director of the United States Patent and Trademark Office*